United States Patent [19]

Hansen

[11] Patent Number: 5,158,661
[45] Date of Patent: Oct. 27, 1992

[54] ELECTROPHORESIS TEMPERATURE CONTROL APPARATUS

[75] Inventor: Michael E. Hansen, Pewaukee, Wis.

[73] Assignee: Fotodyne Incorporated, New Berlin, Wis.

[21] Appl. No.: 674,540

[22] Filed: Mar. 22, 1991

[51] Int. Cl.[5] .......................................... G01N 27/26
[52] U.S. Cl. ............................. 204/299 R; 204/182.8; 204/274
[58] Field of Search .................. 204/182.8, 299 R, 274

[56] References Cited

U.S. PATENT DOCUMENTS

| 4,024,046 | 5/1977 | Lupinski et al. | 204/300 EC |
|---|---|---|---|
| 4,048,049 | 9/1977 | Hoefer | 204/182.8 |
| 4,362,612 | 12/1982 | Bier | 204/301 |
| 4,561,961 | 12/1985 | Hofmann | 204/299 R |
| 4,612,106 | 9/1986 | Kromer et al. | 204/299 R |
| 4,624,768 | 11/1986 | Yoshida et al. | 204/299 R |
| 4,657,655 | 4/1987 | Smoot et al. | 204/299 R |
| 4,735,697 | 4/1988 | Burton | 204/182.8 |
| 4,834,862 | 5/1989 | Breiner et al. | 204/301 |
| 4,897,169 | 1/1990 | Bier et al. | 204/183.2 |
| 4,898,658 | 2/1990 | Karger et al. | 204/299 R |
| 4,909,920 | 3/1990 | Sarrine et al. | 204/299 R |

Primary Examiner—John Niebling
Assistant Examiner—David G. Ryser
Attorney, Agent, or Firm—Michael, Best & Friedrich

[57] ABSTRACT

Electrophoresis apparatus comprising an electrophoresis device including an electrophoresis chamber for containing a solid matrix electrophoresis medium and an electrically conductive fluid, a structure for establishing an electric field in the fluid and in the medium, and a structure including a Peltier element for circulating the fluid through the chamber and for removing heat from the fluid.

9 Claims, 3 Drawing Sheets

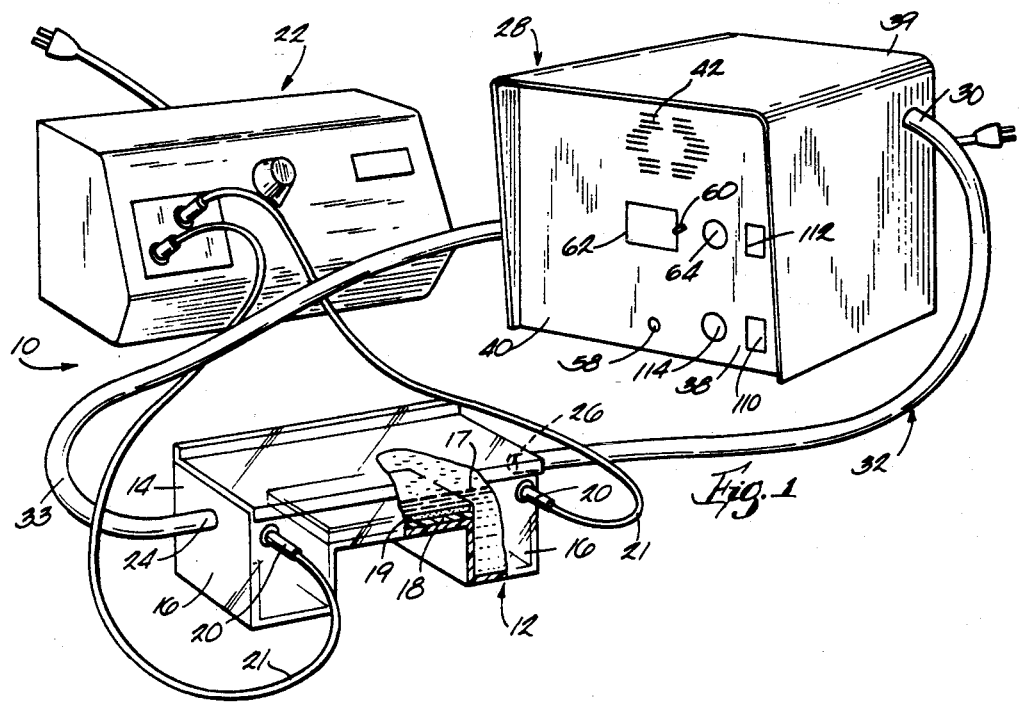

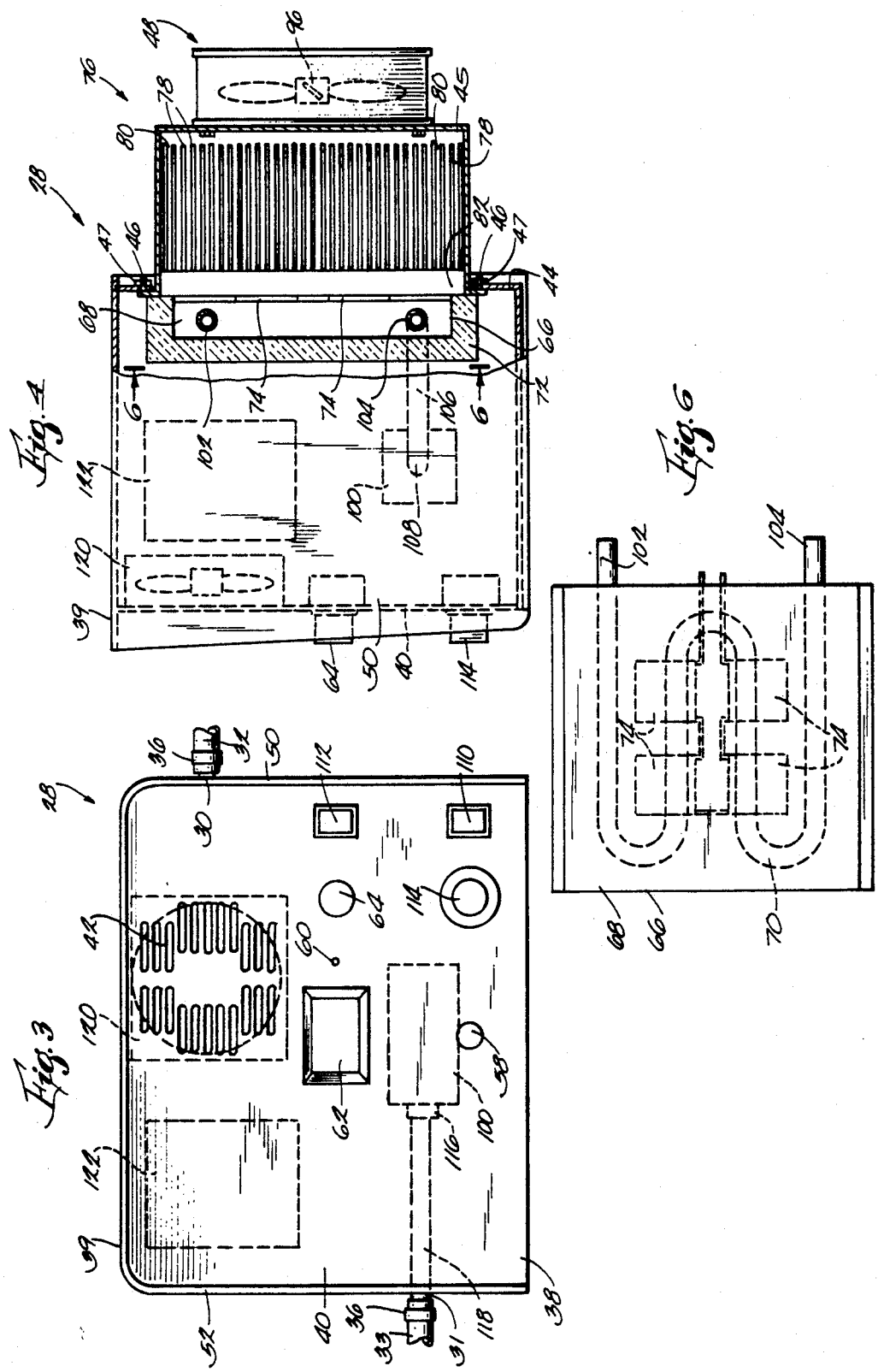

ELECTROPHORESIS TEMPERATURE CONTROL APPARATUS

FIELD OF THE INVENTION

This invention relates generally to electrophoresis, and more particularly to a buffer temperature control and circulation system for use in conjunction with electrophoresis.

BACKGROUND OF THE INVENTION

Electrophoresis is an essential tool for analytical molecular biology, and is increasingly being used for the purification of various kinds of chemical substances. Electrophoretic separations are generally accomplished by establishing an electric field through a conducting medium containing charged particles, with the result that the charged particles are induced to migrate within the electrical field and through the conducting medium.

When the conducting medium is a porous solid or colloidal mixture, the resulting migration of the charged particles through this solid matrix can result in their separation by size, due to the differential migrating rates of variously sized particles through such a medium. Agarose gel electrophoresis is an example of electrophoretic separation in this manner, and is most commonly used to size and separate nucleic acids into discrete bands within the gel for analysis. The gel forms the solid matrix where the separation occurs and is usually generally surrounded by a buffered electrolyte containing solution, or buffer, which evenly conducts the electric field from the electrodes through the gel, and also serves in absorbing and dissipating heat from the operation.

The separation of other biochemical components can be accomplished by this same technique or by any of a wide variety of similar techniques. Proteins or nucleic acids can be separated by size through the use of sodium dodecyl sulfate polyacrylamide gel electrophoresis (SDS-PAGE). Solid matrix gels are also useful in techniques for separation by the charge of the sample particles alone, such as in isoelectric focusing, where the electrical field generates a pH gradient within a gel and the sample particles migrate differentially, dictated by their dissimilar charges, to discrete points along this pH gradient. This is most commonly utilized in separating proteins by their isoelectric points.

In any case, the application of an electrical field consequently results in the generation of Joule heat, the heat resulting from the passage of an electric current through a resistance, and in those applications utilizing electric fields of higher amperages and voltages the amount of such heat can be considerable. This additional heat can have an adverse affect on the efficiency of the electrophoretic separation, and in extreme cases can result in the partial melting of all or portions of the matrix material. Further the substances being electrophoretically separated may be degraded to the point of loss of biochemical activity by the heat so generated. This is a particular problem in those applications where the electrophoretic separation is conducted rapidly by utilizing a more powerful electrical field, or in pulsed field or alternating field electrophoresis techniques. These last techniques generate higher amounts of heat for the same amount of separation achieved, due to the varying and alternating directions of the applied electrical fields. The heat dissipated into the conducting fluid and the electrophoresis medium increases in relation to the amount of applied electrical power.

Thus, if one wishes to use higher electrical power levels to decrease the time for a given electrophoretic separation, or if one is utilizing the pulsed field or alternating field electrophoretic techniques, it is important to address the issue of heat generation within the separation medium or the buffer which is in contact with both the medium and the electrodes. Various apparatus have been proposed for dissipating this heat, such as cooling the buffer by chilling the buffer wells, or in some cases cooling the solid matrix, or gel plate, directly. The primary and most satisfactory method thus far has been to cool the buffer by passing it through tubing immersed in a chilled environment, such as through a bucket of ice water or the like. Heat is exchanged between the liquids across the tubing, and the buffer that is ultimately returned to the electrophoresis chamber has a greatly reduced temperature. Such a method, however, requires a number of different bulky components, which makes the overall operation both cumbersome and requires the utilization of a large amount of bench space. It is also difficult to control the amount of cooling in such a system. Commonly utilized plastic tubing is not known for its heat exchanging ability.

SUMMARY OF THE INVENTION

Controlling the temperature of electrophoresis buffering solution, or buffer, can have an important beneficial effect on the separation achieved through the matrix medium. With more sophisticated electrophoresis techniques utilizing higher voltage powers it becomes increasingly important to be able to accurately control the temperature of the buffer. A circulating buffer maintained at a fairly constant temperature would greatly assist in keeping conditions for electrophoresis optimal, and would aid in keeping the matrix medium where the separation or purification of the substances occurs at an acceptable temperature level.

It is an object of the invention, therefore, to provide a buffer temperature control system which can circulate and maintain electrophoresis buffer at a constant temperature.

Another object of the invention is to provide such a system which has flexible temperature controls which can be used to accurately maintain a chosen temperature for the buffer.

A further object of the invention is to provide such a system which is available in compact form, consolidating the circulation, heat exchange and control mechanisms into one unit.

A still further object of the invention is to provide such a unit which will occupy very little bench space.

Another object of the invention is to provide such a system in which solid state components are utilized to improve both the ruggedness and the compactness of the resulting unit.

A further object of the invention is to provide such a system which utilizes Peltier elements or thermoelectric modules in order to accomplish more accurate and rapid adjustments to the buffer temperature.

A still further object is to provide a temperature control system in which the operation is reversible so that heat can be removed from or supplied to the buffer circulating through the unit.

The electrophoresis temperature control and circulation system of the invention comes as a compact unit, consolidating the functions of buffer circulation and buffer cooling or heating along with all of the necessary controls and readouts. The buffer is circulated through a metal heat exchanger which can be either cooled or heated by thermoelectric modules which are preferably sandwiched between the heat exchanger and a forced convection cooled heat sink. In alternative embodiments of the invention other types of heat sinks could be employed. All of the material in contact with the buffer within the heat exchanger can be of stainless steel or other corrosion resistant tubing. A pump within the temperature control and circulation unit is operated by a variable speed control. The pump is user programmable by means of a numbered dial provided on the front panel.

During operation, the buffer is circulated through the heat exchanger and heat is either removed to or supplied from the heat sink. The supply of the electric current to the thermoelectric modules is temperature controlled. This temperature control can be accomplished easily through use of a simple on/off system where the thermoelectric modules are fully powered when the actual temperature deviates from the set point. This set point temperature is then programmable by means of a dial provided on the front panel.

The set point temperature may be displayed on the front of the panel through the use of a three digit LED display. The actual temperature may come from one of two sensors. In the standard configuration the actual temperature is read from the buffer as it enters the inlet of the unit. The alternative method utilizes a remote temperature sensor which can be placed within the electrophoresis chamber itself in order to get accurate readings of the buffer temperature within the portion of the device where the samples are separated.

Because thermoelectric modules are used as the heat pump, the overall unit is composed largely of solid state materials, with only the fluid pump and the fans having movable parts. The use of an oscillating pump allows for fairly compact space utilization and relatively quiet operation overall. The thermoelectric modules also make possible rapid and accurate temperature adjustments to the buffer.

The resulting electrophoresis buffer temperature control and circulation system is ideal for use with pulsed field or alternating field electrophoretic techniques, or for use with any electrophoretic technique where the user desires to speed up the rate of separation by utilizing higher voltages. In the latter case, the unit can help in reducing the running times for standard electrophoretic techniques by rapidly and efficiently cooling and circulating the buffer and thus increasing the acceptable levels of power which can be supplied. The Joule heat generated by the increased voltages is effectively dissipated to the external environment, keeping the overall temperature low, while the circulation prevents the creation of hot spots or distortions within the electrophoresis medium.

Heat can also be supplied to a circulating buffer, when needed. As but one example, this could be desirable when electrophoresis is to be performed in a refrigerated room or the like.

The present unit accomplishes this without bulky refrigeration units, cooling coils or ice baths, and will occupy less than one square foot of bench space, with additional air space needed for proper exhaust ventilation.

BRIEF DESCRIPTION OF THE DRAWINGS

FIG. 1 is a perspective view of an electrophoresis system in operation, with an electrophoresis chamber shown attached to both a power source and to the buffer temperature control and circulation unit of the invention.

FIG. 2 is a block diagram showing the operational relationship of the various components of the buffer temperature control and circulation unit and the relationship of its components to an electrophoresis system.

FIG. 3 is a front view of the unit of the invention demonstrating the location of the readouts and controls, and partially disclosing the internal locations of the various components.

FIG. 4 is a side view of the unit, again partially displaying the locations of certain of the internal components.

FIG. 6 is a plan view along 6—6 of FIG. 4, showing the heat exchange element utilized within the unit in relation to the Peltier elements and the block of the heat sink.

Figure 5:
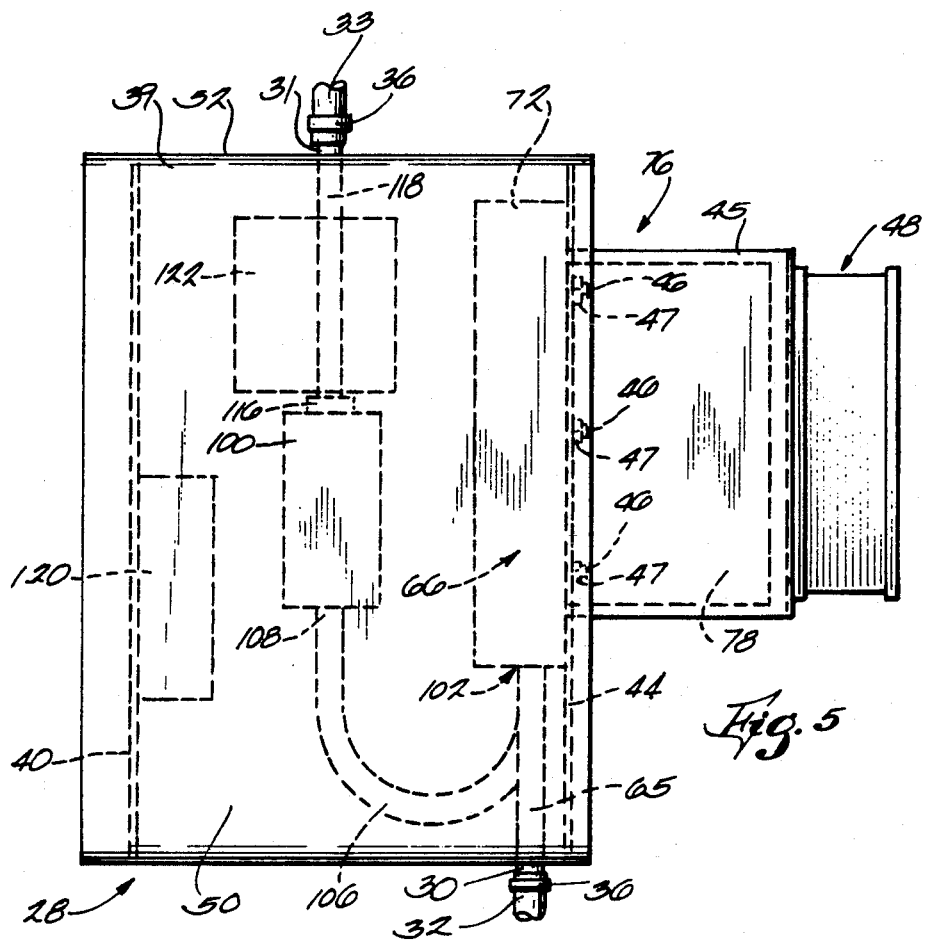
FIG. 5 is a plan view of the unit, partially disclosing internal connections of the components.
Figure 7:
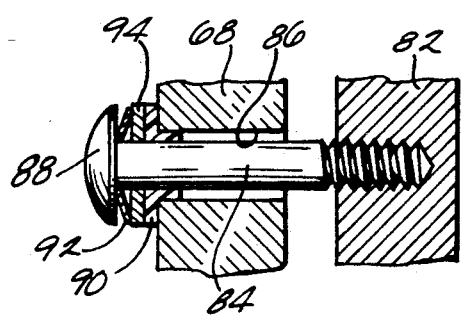
FIG. 7 is an enlarged view of the electrically insulated screw attachments between the heat sink and heat exchange elements.

Before one embodiment of the invention is explained in detail, it is to be understood that the invention is not limited in its application to the details of construction and the arrangement of components set forth in the following description or illustrated in the drawings. The invention is capable of other embodiments and of being practiced or carried out in various ways. Also, it is to be understood that the phraseology and terminology used herein is for the purpose of description and should not be regarded as limiting.

DESCRIPTION OF THE PREFERRED EMBODIMENT

Electrophoresis apparatus 10 embodying the invention is illustrated in the drawings. The electrophoresis apparatus 10 includes (See FIG. 1) an electrophoresis device 12 such as is most commonly utilized in separating nucleic acids through an agarose gel matrix. This device includes an electrophoresis chamber 14 with wells 16 for containing an electrically conducting fluid, generally a buffered electrolyte solution, or buffer 17. The chamber 14 also includes a platform 18 which is located between the wells 16 and which supports a solid matrix electrophoresis medium 19. The medium would most commonly be a gel made up of an electrolyte solution and agarose, through which electrophoretic separation occurs. Other solid matrix materials for use in electrophoresis include other gel or colloidal mixes, fibrous materials, or suitably porous ceramics, to name a few. The device 12 also includes means for establishing an electric field in the buffer 17 and in the gel 19. Such means preferably includes electrical attachments 20 and lead wires 21 connecting the attachments 20 to a power supply 22. The device 12 also includes an inlet 24 and an outlet 26, both of which communicate with the chamber 14. Such a device is disclosed in U.S. Pat. No. 4,657,655, which is assigned to the assignee hereof and which is incorporated herein by reference.

The apparatus 10 also comprises means for circulating the buffer solution 17 through the chamber 14 and for transferring heat relative to the solution 17. Such means preferably includes a temperature control and circulation unit 28. The unit 28 has (see FIGS. 3 and 5) an inlet 30 and an outlet 31 and communicates with the device 12 through conduits 32 and 33. The conduits 32 and 33 are preferably lengths of insulated flexible tubing. As shown in FIG. 1, the conduit 32 connects the inlet 30 of the unit 28 to the outlet 26 of the electrophoresis device 12, and the conduit 33 connects the outlet 31 of the unit 28 to the inlet 24 of the device 12. Small clamps 36 (FIG. 3) secure the conduits 32 and 33 to the inlet 30 and outlet 31 of the unit 28.

In FIG. 2, the workings of the buffer temperature control and circulation unit 28 are disclosed by means of a block diagram. Those components internal to the unit are enclosed by the dotted line within FIG. 2. Any electrophoresis device or buffer source which has a chamber with continuous flow from inlet to outlet ends could be utilized with the unit 28.

FIGS. 3, 4 and 5 demonstrate the general locations within the unit of the various components, through front, side and top views respectively. These are the same components as are disclosed as blocks within FIG. 2.

The unit 28 includes rigid housings 38 and 39. The top housing 39 can be detached from the bottom housing 38 to expose the internal workings of the unit 28. The bottom housing 38 has a front panel 40 which supports various controls and readouts, as well as an air outlet 42 (FIGS. 1 and 3) for circulation of internal air. An air inlet at the bottom of the housing 38 is not shown. Housing 38 has (see FIG. 4) a back panel 44 with a separate housing or support bracket 45 attached thereto by a plurality of studs 46, which pass through holes in the back of the housing 38 and are secured thereto by nuts 47. A fan housing 48 attaches to the back of this separate housing 45. The top housing 39 has (see FIG. 3) side panels 50 and 52. The side panel 50 has therein the inlet 30, while the opposite side panel 52 has therein the outlet 31.

The temperature of the circulating buffer 17 can be detected as it enters the unit 28. A temperature sensor 54 (not depicted in FIGS. 1 and 3-7 but included in the block diagram of FIG. 2) can be epoxied near the inlet 30, preferably to a length of stainless steel tubing through which the buffer 17 flows. A remote sensor 56 (again represented in FIG. 2) can be utilized to measure the buffer temperature at a location within the electrophoresis chamber 14. The front panel 40 includes (see FIGS. 1 and 3) a plug 58 for connecting such a remote sensor 56. The sensing portion of the remote sensor 56 can be variously located as needed within the electrophoresis chamber 14.

The actual temperature may then be recorded or displayed, the illustrated embodiment incorporating means for selectively displaying either the actual temperature as detected or a predetermined temperature. The front panel 40 also has a toggle switch 60 which sets the display for one or the other temperature. In the preferred embodiment the front panel 40 also has displaying means 62 in the form of a three digit LED.

When the remote sensor 56 is attached to the remote plug 58 the remote sensor automatically overrides the internal sensor and the temperature of the former is displayed. In either case, the temperature is also fed to a controlling means 63 (FIG. 2) in the form of a circuit board, which aids in maintaining the temperature substantially at the set temperature, by a mechanism which is described hereafter. Means for predetermining the set point temperature include a user programmable dial 64 on the front panel 40, making the set point temperature selectively variable.

Inside the unit 28, as shown in FIGS. 5 and 6, the buffer 17 passes through a heat transfer device or heat exchanger 66, in the illustrated embodiment going from the inlet 30 of the unit 28 through an internal conduit 65 to the heat transfer device. The heat exchanger 66, as best illustrated in FIG. 6, consists of a block 68 of a material with high thermal conductivity, preferably aluminum, with an internal length of tubing 70, preferably of a corrosion-resistant material, preferably stainless steel. Such a preferred device can be purchased from EG & G Wakefield Engineering of Wakefield, Mass., their Part No. 108-20. As buffer 17 passes through the stainless steel tubing 70 of the aluminum block 68, the aluminum conducts the heat and thereby works to equilibrate the temperature, by rapidly absorbing excess heat, or donating heat to the buffer. The heat exchanger 66 is separated from the interior environment of the unit 28 by a layer of insulation 72 (FIG. 5), such as a closed cell polyurethane foam.

As shown in FIGS. 4 and 6, a plurality of Peltier elements or thermoelectric modules 74, four in the illustrated embodiment, are arrayed with surfaces adjacent the back surface of the heat exchanger 66. The thermoelectric modules 74 have their own DC power supply, with a transformer circuit board 75 (not depicted except within FIG. 2) for converting AC power to DC power. The application of DC power of a certain polarity to the modules 74 causes heat pumping such that one of the surfaces is heated while the opposite surface is cooled. The cooling and warming at opposite ends of a thermoelectric couple is known as the Peltier effect, and results from the direct current passing around a circuit formed from two dissimilar metals, or from a metal and a semiconductor. The result is that one junction gives off heat and is cooled and the other absorbs heat and becomes warm. When the DC power supply to the thermoelectric modules is on, heat is absorbed at one surface of the device which cools that end, while heat is rejected at the other, where the temperature rises. Consequently, the cooling and heating surfaces of a thermoelectric module can be switched through simply reversing the polarity of the DC current supplied to the modules. In this manner the thermoelectric modules can be used to alternatively supply heat to the heat exchanger 66, or pull heat away, as is required. The thermoelectric elements currently used are such as can be acquired from Materials Electronics Products Corporation of Trenton, N.J., their Part No. CP1.0-127-05L.

The aluminum block 68 of the heat exchanger 66 efficiently transfers heat between the buffer 17 passing through the tubing 70 of the heat exchanger 66, and the surfaces of the four thermoelectric modules 74. Consequently, heat is rapidly drawn from or supplied to the circulating buffer 17 as it passes through the stainless tubing 70 of the heat exchanger 66.

The surfaces of the thermoelectric modules 74 away from the heat exchanger 66 cool and heat contrary to the surfaces abutting the heat exchanger 66. Inside the housing 45 at the back of the unit is a heat sink 76, which has a surface abutting the surfaces of the thermoelectric modules 74 that are away from the heat exchanger 66. The illustrated heat sink 76 is a high surface area arrangement of a plurality of thin aluminum plates, or fins 78, in parallel. Gaps 80 form between the fins 78, and these gaps 80 open to the sides and to the back. At the front the fins 78 attach to the back of a block of aluminum 82, with the front surface of the block 82 abutting the thermoelectric modules 74. When the surfaces of the modules 74 that abut the heat sink are heating, the heat must be dissipated to the environment. When they are cooling, heat from the environment must be supplied.

The relatively thin modules 74 are thus sandwiched snugly between the aluminum block 82 of the heat sink 76 and the aluminum block 68 of the heat exchanger 66. A plurality of screws 84 (see FIG. 7) are used to hold the aluminum blocks 68 and 82 together. The electrophoresis buffer 17 passing through the heat exchanger 66 contains a voltage, and so these two aluminum bodies 68 and 82 must be electrically isolated from one another. The connecting screws 84 thread into the block 82 of the heat sink 76 but not into the heat exchanger 66, the bore 86 through the block 68 of the heat exchanger 66 having a larger diameter than the screw 84. The screw head 88 is held off of the surface of the block 68 by the use of an insulating shoulder washer 90 about the bore opening. A spring washer 92 and a metal washer 94 finish the arrangement, the spring washer 92 adjacent the screw head 88. The spring washers 92 equalize the pressure over all of the thermoelectric modules 74 in the assembly. The screw attachment is thus arranged to keep the heat sink 76 physically isolated from the heat exchanger 66.

During cooling operation, the fins 78 of the heat sink 76 dissipate heat to the external environment. A fan 96 is located within the small housing 48 at the back of the unit 28, and is used to increase the efficiency of the cooling by continuously circulating air through the gaps 80 of the fins 78. The fan 96 pushes air forward through the gaps 80 of the fins 78, with the air subsequently exiting the gaps 80 laterally. The fan 96 is wired in such a manner that it automatically goes on when power is supplied to the modules 74. The overall operation thus functions in transferring heat between buffer 17 circulating through the heat exchanger tubing 70 and the air of the external environment.

Means for pumping the fluid, or buffer 17, from the heat transfer device 66 to the electrophoresis chamber 14 are located within the unit 28, and serve to pull the fluid through the heat exchanger 66. Such means preferably includes a fluid pump 100. The heat exchanger 66 (see FIGS. 3-5) has an inlet 102 which is connected to the inlet 30 of the unit 28, and an outlet 104 where an internal conduit 106 leads the buffer 17 to the pump 100. The pump 100 has an inlet 108 communicating with the conduit 106. In the preferred embodiment the pump 100 is an oscillating fluid pump. Such a pump is available from Gorman-Rupp Industries of Bellville, Ohio, Pump Model No. 14825-601. A programmable pump speed controller 109 (see FIG. 2), preferably a circuit board controlling the phase of the halfway rectified AC voltage supplied to the pump, controls the pump speed. The pump 100 has (see FIG. 3) an on/off switch 110 and the thermoelectric modules 74 have an on/off switch 112, both found on the front panel 40 of the unit 28. These switches 110 and 112 are in series in such a manner that the modules 74 will not be powered unless the fluid pump 100 is running. This reduces the chance that buffer 17 inadvertently left in the tubing 70 of the heat exchanger 66 could be frozen or overheated by the action of the modules 74.

The speed of the pump 100 is selectively variable. The pump speed controller 109 can be programmed through a numbered dial 114 which is located on the front panel 40 of the unit 28. The fluid pump 100 has (see FIG. 3) an outlet 116 connected to the unit outlet 31 by an internal conduit 118, preferably insulated. A fan 120 (FIG. 4) internal to the unit 28 pushes air out through the opening 42 in the front panel 40. Fresh air circulates up from an inlet (not depicted) in the bottom of the housing 38, and is used to dissipate the heat of the internal electronics, and particularly the heat generated by operation of the pump 100. The front fan 120 switches on automatically with the fluid pump 100. The pump 100 is preferably attached to the bottom of the unit housing 38, where vibrations will be less noticeable than if attached to the front or side of the housing 38. An internal power transformer 122 is attached to the front panel 40 of the housing 38, and it and all internal wiring (not illustrated) are located above the pump 100 so that condensation from the pump 100 will not drip onto electronic circuitry.

The unit 28 also includes means for maintaining the temperature of the fluid substantially at a predetermined temperature. This means is preferably the above-mentioned means 63 (FIG. 2), which is preferably a simple on/off type arrangement. For instance, in operating to cool a buffer, the power to the modules 74 will be fully on when the actual temperature is above the set point temperature, and fully off when the actual temperature is below that of the set point temperature. In heating a buffer the polarity to the modules 74 is reversed, and the modules 74 are fully powered when the temperature falls below the set temperature. Alternatively, the temperature could be controlled through the use of a microprocessor (not shown) which would variably control the DC current such that as the actual temperature approaches the set point temperature the current is correspondingly reduced, the current shutting off completely when the actual temperature equals the set temperature, and reversing when the actual temperature crosses over the set point temperature. The dial 64 provided on the front of the unit is for setting the set point temperature.

The reversible nature of the temperature control feature of the unit 28 is preferably controlled by a circuit board (not shown), which flips the polarity of the current to the modules 74 depending upon whether the temperature of the buffer 17 is above or below that of the set temperature. In the cooling mode, when the set temperature is below the actual buffer temperature, the polarity is such that the surfaces of the thermoelectric modules nearest the heat exchanger are cooled while their opposite surfaces give off heat to the heat sink. When the buffer temperature falls below the set temperature the polarity is reversed, causing the surfaces of the thermoelectric modules 74 nearest the heat exchanger 66 to absorb heat and get hot, while the sides adjacent the heat sink 76 cool down, thus taking heat from the air and passing it to the circulating buffer 17. Thus modulating the current to the modules 74 means that the unit 28 can stabilize a buffer temperature either above or below that of ambient air.

In operation the unit 28 is placed on a flat level surface in proximity to the electrophoresis device 12 with which it is to be connected. About one foot of space around the back of the unit 28 must be free to provide proper ventilation for the heat sink 76. With both the fluid pump 110 and heat pump 112 switches in the off position, the unit 28 is plugged into a properly grounded three conductor outlet.

For attaching the unit 28 to the electrophoresis chamber 14, it is preferred that foam insulation tubing be provided for surrounding the tubings 32 and 33 that will be attached to the inlet 30 and outlet 31 of the unit 28. Approximately one watt of heat pumping power is lost per every inch of noninsulated exposed tubing. The insulated tubings 32 and 33 are connected as previously described and as depicted in the drawings, utilizing clamps 36 to secure the connections against leaking. Once the electrophoresis chamber 14 has been filled with buffer 17, the pump 100 of the unit is primed by turning the pump 100 on. Air bubbles are purged from the system with the pump speed at its maximum rate for a short time, and after the air bubbles have been purged the pump 100 is returned to off. It is important when running the unit to make sure that there is sufficient buffer 17 to completely prime the internal tubing of the unit and still allow the gel 19 within the electrophoresis chamber 14 to be completely covered with buffer 17.

The temperature adjustment is simply a matter of turning the adjustment dial 64 on the front of the unit to the desired set point temperature, which is displayed on the digital readout 62 while the toggle switch 60 on the front panel 40 is set for displaying the set temperature. The toggle switch 62 at the front panel of the unit can then be switched to display the actual temperature.

The correct pump speed for a given application will depend upon the amount of heat that is lost into the electrophoresis chamber, and upon the wattage of the applied electrical field. In general, it is preferred to operate the pump 100 at the lowest speed necessary for maintaining the desired set point temperature, although slightly higher pump speeds will be acceptable. Higher wattages in general require higher pump speeds, while at lower wattages it is sometimes preferable to use lower speeds when possible, as too great an excess in the pump speed can create heat and work against the cooling. Circulation works to maintain a more uniform temperature throughout the system, so increasing the pump speed will aid in keeping the electrophoresis chamber uniformly cool. Trial and error will sometimes be necessary to determine the ideal pump setting for a given electrophoresis system or given running conditions. Additionally, care must be taken that the gel 19 not be loosened and lifted from its plate by a high flow rate, which is more likely to happen with a thin or flimsy gel.

Also, the greater the difference between the desired temperature and the ambient temperature the greater the need for a proper speed for maintaining a given temperature, as the pump at high speed can add heat to the system. For a given thermoelectric arrangement and a given pump capacity and speed control it is possible to work out general preferred pump speed settings for given conditions.

Once a set point temperature and pump speed have been determined, the pump speed dial 114 is set to zero, in essence turning the pump 100 off, while the solidified gel 19 is placed in the electrophoresis chamber 14 and the gel sample wells are loaded. The buffer 17 should completely cover the gel 19, as this allows the smooth flow of the circulating buffer 17 between buffer wells 16. Once the samples have been loaded into the gel 19, voltage is applied from the power supply 22 while the fluid pump 100 remains off, in order to ensure that the sample will migrate safely into the gel 19 without any danger of dispersal of the sample by flowing buffer 17. The fluid pump speed then is slowly adjusted upwards to a predetermined dial setting, or until it is clear that the thermoelectric elements 74 and the heat exchanger 66 are pulling off all the generated heat. This will be reflected in a consistent readout on the LED 62 while the toggle switch 60 is set to record the actual temperature.

Electrophoresis of the sample then progresses uninterrupted until completion. Upon termination, power to the device 12 is shut off, and the lead wires 21 to the electrophoresis device 12 are disconnected. The pump speed switch 110 and the heat pump switch 112 are then turned to off. Once the electrophoresis device 12 is disconnected from the unit 28, the unit 28 still needs to be purged of buffer 17. It is preferable that the inlet tubing be disconnected from the electrophoresis device 12 and that the pump 100 be allowed to run in order to purge the buffer 17 remaining within the unit 28.

After the buffer 17 has been completely purged, distilled water is preferably pumped through the system as well. The use of distilled water as a final rinse prevents the build up of buffer precipitates on the internal components. The end of the tubing 32 attached to the unit inlet 30 is placed in a beaker of distilled water and the tubing 33 attached to the unit outlet 31 is placed in an empty beaker and the fluid pump 100 is turned on. About 1 liter of distilled water is preferably passed through the unit 28 in order to ensure complete purging from the system of traces of the buffer 17. It is especially important to so rinse the unit 28 prior to a long storage period, while if the unit 28 is going to be used repeatedly it may not be necessary to rinse with distilled water after every use.

Various features of the invention are set forth in the following claims.

I claim:

1. Apparatus for use with an electrophoresis device including an electrophoresis chamber for containing a solid matrix separation medium and an electrically conductive fluid that is not a separation medium and that is in heat exchanging relation with said separation medium, the chamber having an inlet and an outlet, and means for establishing an electric field in the fluid and in the medium, said apparatus comprising means for circulating the fluid through the chamber and for removing heat from the fluid, said circulating and removing means including a heat transfer device including a block having high thermal conductivity and having therein tubing which is corrosion resistant, which conducts the fluid, and which has an inlet and an outlet, a conduit communicating between the chamber outlet and said tubing inlet, a heat sink, a Peltier element located between said block and said heat sink, a fan for blowing air over said heat sink, a variable speed fluid pump having an inlet communicating with said tubing outlet, and having an outlet, a conduit communicating between said pump outlet and the chamber inlet, and means for maintaining the temperature of the fluid substantially at a predetermined temperature, said maintaining means including means for sensing the temperature of the fluid, means for supplying power to said Peltier element when the temperature of the fluid is different from said predetermined temperature, and means for selectively varying said predetermined temperature.

2. Apparatus for use with an electrophoresis device for containing a solid matrix separation medium and including a chamber for containing a fluid that is not a separation medium and that is in heat exchanging relation with said separation medium, the chamber having an inlet and an outlet, and means for establishing an electric field in the medium, said apparatus comprising means for circulating the fluid through the chamber and for removing heat from the fluid, said circulating and removing means including a heat transfer device including a block having high thermal conductivity and having therein tubing which is corrosion resistant, which conducts the fluid, and which has an inlet and an outlet, a conduit communicating between the chamber outlet and said tubing inlet, a heat sink, a Peltier element located between said block and said heat sink, means for transferring heat relative to said heat sink, a variable speed fluid pump having an inlet communicating with said tubing outlet, and having an outlet, a conduit communicating between said pump outlet and the chamber inlet, and means for maintaining the temperature of the fluid substantially at a predetermined temperature, said maintaining means including means for sensing the temperature of the fluid, means for causing current flow through said Peltier element in one direction when the temperature of the fluid is above said predetermined temperature, and means for selectively varying said predetermined temperature.

3. Apparatus a set forth in claim 2 wherein said means for transferring heat relative to said heat sink includes a fan.

4. Apparatus as set forth in claim 2 wherein said fluid is a buffer solution, and wherein said separation medium and said buffer solution are located in said chamber.

5. Apparatus as set forth in claim 2 wherein said maintaining means includes means for causing current flow through said Peltier element in the opposite direction when the temperature of the fluid is below said predetermined temperature.

6. Electrophoresis apparatus comprising an electrophoresis device for containing a solid matrix separation medium and including a chamber for containing a fluid that is not a separation medium and that is in heat exchanging relation with said separation medium, said chamber having an inlet and an outlet, and means for establishing an electric field in the medium, and means for circulating the fluid through said chamber and for removing heat from the fluid, said circulating and removing means including a heat transfer device including a block having high thermal conductivity and having therein tubing which is corrosion resistant, which conducts the fluid, and which has an inlet and outlet, a conduit communicating between said chamber outlet and said tubing inlet, a heat sink, a Peltier element located between said block and said heat sink, means for transferring heat relative to said heat sink, a variable speed fluid pump having an inlet communicating with said tubing outlet, and having an outlet, a conduit communicating between said pump outlet and said chamber inlet, and means for maintaining the temperature of the fluid substantially at a predetermined temperature, said maintaining means including means for sensing the temperature of the fluid, means for causing current flow through said Peltier element in one direction when the temperature of the fluid is above said predetermined temperature, and means for selectively varying said predetermined temperature.

7. Apparatus a set forth in claim 6 wherein said means for transferring heat relative to said heat sink includes a fan.

8. Apparatus as set forth in claim 6 wherein said fluid is a buffer solution, and wherein said separation medium and said buffer solution are located in said chamber.

9. Apparatus as set forth in claim 6 wherein said maintaining means includes means for causing current flow through said Peltier element in the opposite direction when the temperature of the fluid is below said predetermined temperature.

* * * * *